United States Patent
Kwon et al.

(10) Patent No.: US 11,937,921 B2
(45) Date of Patent: Mar. 26, 2024

(54) OPTICAL APPARATUS AND APPARATUS FOR ESTIMATING BIO-INFORMATION USING THE SAME

(71) Applicant: SAMSUNG ELECTRONICS CO., LTD., Suwon-si (KR)

(72) Inventors: Bok Soon Kwon, Seoul (KR); Woochang Lee, Anyang-si (KR); So Young Lee, Daejeon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 408 days.

(21) Appl. No.: 17/215,580

(22) Filed: Mar. 29, 2021

(65) Prior Publication Data

US 2022/0125350 A1 Apr. 28, 2022

(30) Foreign Application Priority Data

Oct. 23, 2020 (KR) .................. 10-2020-0138300

(51) Int. Cl.
*A61B 5/1455* (2006.01)
*A61B 5/00* (2006.01)
*A61B 5/145* (2006.01)

(52) U.S. Cl.
CPC ...... *A61B 5/14532* (2013.01); *A61B 5/14546* (2013.01); *A61B 5/14551* (2013.01); *A61B 5/4845* (2013.01); *A61B 5/4875* (2013.01); *A61B 5/6826* (2013.01); *A61B 2562/0247* (2013.01)

(58) Field of Classification Search
CPC . A61B 5/0205; A61B 5/1455; A61B 5/14551; A61B 5/14552; A61B 5/14532; A61B 5/14546; A61B 5/4845; A61B 5/4875; A61B 5/6826; A61B 5/6843; A61B 2562/0233; A61B 2562/0247
See application file for complete search history.

(56) References Cited

U.S. PATENT DOCUMENTS 4,513,751 A * 4/1985 Abe ............... A61B 5/1455
600/479
5,077,476 A * 12/1991 Rosenthal .......... A61B 5/1455
250/339.04

(Continued)

FOREIGN PATENT DOCUMENTS

JP 4896874 B2 3/2012
KR 10-2008-0103503 A 11/2008
KR 10-0871074 B1 11/2008

*Primary Examiner* — Chu Chuan Liu
(74) *Attorney, Agent, or Firm* — Sughrue Mion, PLLC

(57) ABSTRACT

An optical apparatus for non-invasively measuring a bio-signal is provided. The optical apparatus may include an interface housing including: a guide part defined by an interior space of the interface housing and configured to guide an object to a measurement position; and a pressurizing part configured to induce congestion of a second portion of the object by pressing a first portion of the object when the object is disposed within the guide part; and a measurer including: a light source provided on an upper side of the interface housing and configured to emit light to the second portion of the object when the object is at the measurement position; and a detector configured to measure a bio-signal from the second portion by detecting light scattered or reflected from the second portion.

17 Claims, 13 Drawing Sheets

(56) References Cited

U.S. PATENT DOCUMENTS

| | | | |
|---|---|---|---|
| 5,370,114 A | 12/1994 | Wong et al. | |
| 5,436,455 A | 7/1995 | Rosenthal et al. | |
| 5,638,818 A * | 6/1997 | Diab | A61B 5/6826 |
| | | | 600/479 |
| 7,761,129 B2 | 7/2010 | Van Der Voort et al. | |
| 8,306,593 B2 | 11/2012 | Hwang et al. | |
| 8,452,365 B2 | 5/2013 | Rebec et al. | |
| 2005/0209514 A1 * | 9/2005 | Oshima | A61B 5/14532 |
| | | | 600/310 |
| 2005/0272987 A1 | 12/2005 | Kiani-Azarbayjany et al. | |
| 2007/0027373 A1 | 2/2007 | Xie | |
| 2007/0060844 A1 | 3/2007 | Alvarez-Icaza et al. | |
| 2007/0161877 A1 | 7/2007 | Arai et al. | |
| 2009/0060296 A1 | 3/2009 | Mainguet | |
| 2009/0105563 A1 | 4/2009 | Yajima et al. | |
| 2009/0148005 A1 | 6/2009 | Rowe | |
| 2010/0026995 A1 * | 2/2010 | Merritt | A61B 5/6829 |
| | | | 356/222 |
| 2015/0297098 A1 | 10/2015 | Gurfinkel et al. | |
| 2016/0022178 A1 | 1/2016 | Wang | |
| 2016/0317060 A1 * | 11/2016 | Connor | A61B 5/6824 |

\* cited by examiner

OPTICAL APPARATUS AND APPARATUS FOR ESTIMATING BIO-INFORMATION USING THE SAME

CROSS-REFERENCE TO RELATED APPLICATION(S)

This application claims priority to Korean Patent Application No. 10-2020-0138300, filed on Oct. 23, 2020, in the Korean Intellectual Property Office, the entire disclosure of which is incorporated by reference herein for all purposes.

BACKGROUND

1. Field

Example embodiments of the present disclosure relate to an optical apparatus for non-invasively measuring a bio-signal.

2. Description of Related Art

Non-invasive optical apparatuses, using spectroscopic analytic techniques, such as Raman spectroscopy, may improve user convenience as the apparatuses may measure blood components without drawing blood. Particularly, such non-invasive analytic techniques may be used to predict a signal of a blood component by analyzing interstitial fluid present in a dermal layer based on each individual skin spectrum. However, a component measurement method using Raman spectroscopy is disadvantageous in that the signal intensity of a Raman spectrum acquired by light emission is very low. If the exposure time is increased and the number of repeated measurements is increased instead of lowering the light intensity to reduce the influence on the human body by emitted light, a long measurement time is required. However, as the measurement time elapses, a change may occur at an initially set focal position, so that the signal intensity over time decreases compared to an initially measured signal.

SUMMARY

One or more example embodiments provide an optical apparatus for non-invasively measuring a bio-signal.

According to an aspect of an example embodiment, there is provided an optical apparatus including: an interface housing including: a guide part defined by an interior space of the interface housing and configured to guide an object to a measurement position; and a pressurizing part configured to induce congestion of a second portion of the object by pressing a first portion of the object when the object is disposed within the guide part; and a measurer including: a light source provided on an upper side of the interface housing and configured to emit light to the second portion of the object when the object is at the measurement position; and a detector configured to measure a bio-signal from the second portion by detecting light scattered or reflected from the second portion.

The object may be a finger, the first portion may be a fingertip, and the second portion may be a nailfold.

The pressurizing part may include: a plate configured to contact the first portion of the object; and an elastic member that is connected to the plate and configured to deform as the first portion presses the plate.

The plate may be configured to contact at least 50% of a cross-sectional area of the first portion.

The elastic member may have an elastic coefficient that allows the object to apply a force of at least 3 Newtons to the plate.

The interface housing may further include a braking part configured to reduce movement of the plate caused by pressing of the first portion of the object.

The braking part may include: a first locking part connected to the plate and including a projection; and a second locking part connected to the interface housing and having a groove configured to couple to the projection based on the first locking part being moved.

The pressurizing part may include: a plate configured to contact the first portion of the object; and an actuator configured to pressurize the first portion by driving the plate when the first portion is in contact with the plate.

The interface housing may further include a support part configured to support a lateral side of the object when the object is disposed in the guide part.

The support part may include an elastic body configured to deform according to a thickness and a shape of the object.

The measurer may include a hollow body configured to accommodate at least a portion of the second portion that protrudes as the pressurizing part presses the first portion of the object.

A height of the hollow body may be less than a minimum protruding height of the second portion.

The measurer may further include an optical window provided on an upper side of the hollow body and contacting the protruding second portion.

The measurer may be configured to be movable in a horizontal direction or in a vertical direction.

The optical apparatus may further include a sensor provided on a lower side of the interface housing and configured to measure a force or a pressure applied to the second portion by vertical movement of the measurer.

The light source may include a rotatable reflecting mirror configured to emit light to a focal position on the second portion.

The detector may further include a condensing lens configured to condense the light scattered or reflected from the second portion.

According to an aspect of an example embodiment, there is provided an apparatus for estimating bio-information, the apparatus including: an optical apparatus configured to: induce congestion of a second portion of an object by pressing a first portion of the object and measure a bio-signal from the second portion; and a processor configured to estimate the bio-information based on the bio-signal, wherein the optical apparatus includes an interface housing including a guide part defined by an interior space of the interface housing and configured to guide the object to a measurement position, and a pressurizing part configured to induce the congestion of the second portion of the object by pressing the first portion when the object is disposed in the guide part; and a measurer provided on an upper side of the interface housing and configured to measure the bio-signal from the second portion when the object is at the measurement position.

The bio-information may include at least one of oxygen saturation, carotenoids, blood sugar, sugar intake, triglycerides, cholesterol, calories, protein, body water, extracorporeal water, uric acid, and alcohol.

The object may be a finger, the first portion may be a fingertip, and the second portion may be a nailfold.

Other features and aspects will be apparent from the following detailed description, the drawings, and the claims.

BRIEF DESCRIPTION OF THE DRAWINGS

The above and other aspects, features, and advantages of certain example embodiments of the present disclosure will be more apparent from the following description taken in conjunction with the accompanying drawings, in which.

DETAILED DESCRIPTION

Figure 1A:
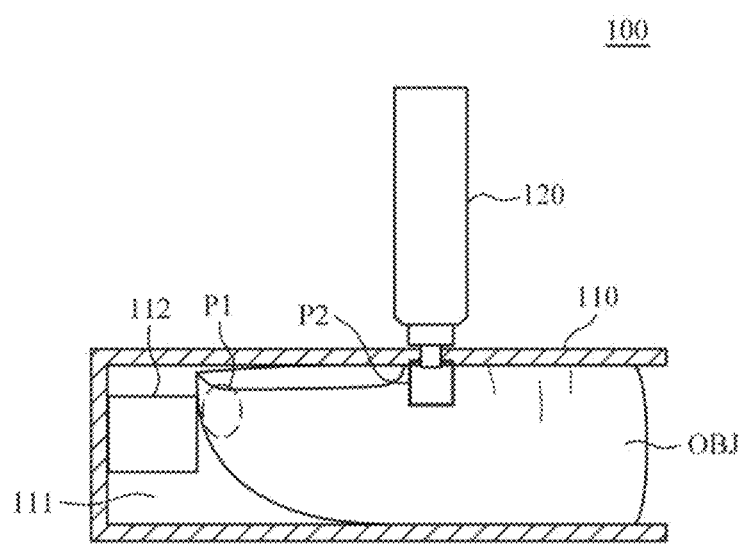
FIG. 1A is a front view showing an example embodiment of an optical apparatus.

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the example embodiments set forth herein. Rather, these example embodiments are provided so that the disclosure will be thorough and complete, and the disclosure will only be defined by the appended claims. Like reference numerals refer to like elements throughout the specification.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and the units may be implemented by using hardware, software, or a combination of hardware and software. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1A is a front view showing an example embodiment of an optical apparatus.

Referring to FIG. 1A, the optical apparatus 100 includes an interface housing 110 and a measurer 120.

The interface housing 110 may be a housing or casing that has an open side end through which an object may be inserted. The interface housing 110 may include a guide part 111 that guides an object OBJ to a measurement position and induces the object to be seated in order to minimize a change in a signal measured by the measurer 120 according to various factors, such as changes in an external measurement environment over the measurement time, changes in the elasticity of the object, or changes in the position of the object. As shown, the guide part 111 may be defined by an interior space of the interface housing 110 into which the object OBJ can be inserted.

The interface housing 110 may include a pressurizing part 112 that induces congestion of a second portion P2 by pressing a first portion P1 of the object OBJ when the object OBJ is inserted into the guide part 111. In this case, the object OBJ may be a finger, the first portion P1 may be a fingertip, and a second portion P2 may be a nailfold. However, aspects of the present disclosure are not limited thereto. For example, the first portion P1 may be a side portion of a finger such as, for example, one or both side portions of the second portion P2. Generally, the nailfold is a suitable position to increase the measurement efficiency of components in the human body. The interface housing 110 of the example embodiment may increase the scattering efficiency of light at the nailfold by lowering the flow rate and increasing the amount of blood circulating in the blood vessel at the nailfold, thereby increasing the volume of the blood vessel.

The measurer 120 may be provided on an upper side of the interface housing 110. At the upper side of the interface housing 110, an opening may be formed in an area where the second portion P2 of the object OBJ is located when the object OBJ is inserted into the guide part 111 and seated at the measurement position. In addition, a lower portion of the measurer 120 may be coupled to the opening.

The measurer 120 may include a light source and a detector. The light source emits light to the second portion P2 of the object OBJ when the object OBJ is seated in the guide part 111 of the interface housing 110, and the detector acquires a bio-signal such as, for example, spectral data, by detecting returning light (hereinafter, referred to as "scattered light") after it has been scattered, reflected, or transmitted from the object OBJ. There is no limitation on the arrangement form of the light source and the detector, and the arrangement form may be an on-axis or off-axis configuration.

The light source may emit light of a predetermined wavelength such as, for example, visible light or infrared light, to the second portion P2 of the object OBJ. However, the light source is not limited thereto, and wavelengths of light emitted by the light source may vary depending on the purpose of measurement and an analysis target. Further, the light source may be a single light emitting body, or may be an array of a plurality of light emitting bodies. In the case where the light source is configured as an array of a plurality of light emitting bodies, the plurality of light emitting bodies may emit light of different wavelengths according to the purpose of measurement, or all the light emitting bodies may emit light of the same wavelength. The light source may be a light emitting diode (LED), a laser diode, a phosphor, or the like. However, these are merely examples, and the light source is not limited thereto. The light source part may include a filter (e.g., clean-up filter, band-pass filter, etc.) for selecting light of a specific wavelength and/or an optical element (e.g., reflection mirror, etc.) for directing the emitted light toward a desired position on the object.

The detector may collect the scattered light from the second portion P2 of the object OBJ. The detector may include a photo diode, a photo transistor (PTr), a charge-coupled device (CCD), or the like. The detector may be a single device, or may be an array of a plurality of devices. Also, the detector may further include a filter (e.g., notch filter, long-pass filter, etc.), a lens (e.g., collection lens, collimating lens, focusing lens, etc.), a fiber, a waveguide, a grating, and the like.

Figure 1B:
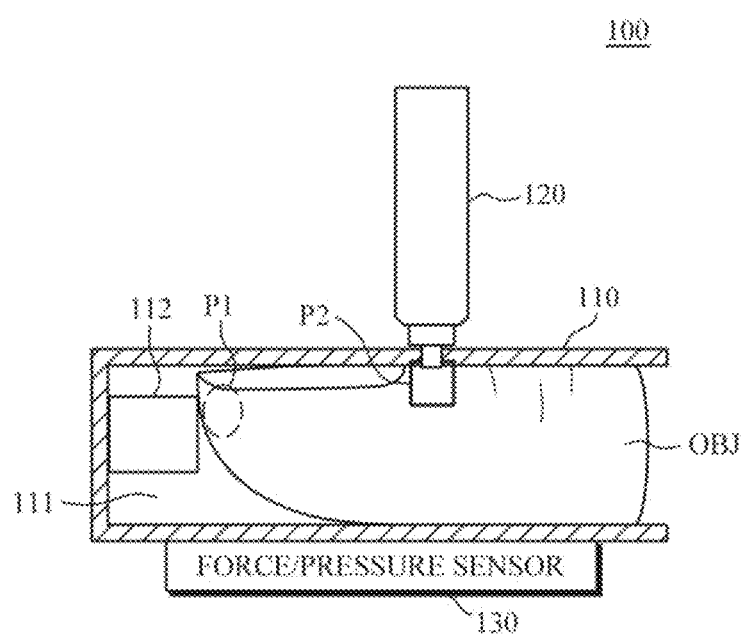
FIG. 1B is a front view showing another example embodiment of an optical apparatus.

FIG. 1B is a diagram showing another example embodiment of an optical device.

Referring to FIG. 1B, the optical apparatus 100 according to another example embodiment may include an interface housing 110, a measurer 120, and a force/pressure sensor 130. The interface housing 110 and the measurer 120 are described above with reference to FIG. 1A.

The force/pressure sensor 130 may be provided on a lower side of the interface housing 110 opposite to the upper side on which the measurer 120 is provided. The force/pressure sensor 130 may measure a force or pressure with which the measurer 120 presses the second portion P2 of the object OBJ from the upper side of the interface housing 110. For example, when the measurer 120 measures the second portion P2 of the object OBJ for an extended period while in contact with the object OBJ, the initially set force or pressure may be changed according to the change in the position of the object OBJ or the change in the elasticity of the second portion P2. Therefore, the force or pressure measured through the force/pressure sensor 130 in this way may be used to maintain the force or pressure that the measurer 120 applies to the object OBJ during the measurement of a bio-signal or may be used to correct the bio-signal on the basis of the change over time in the force or pressure that the measurer 120 applies to the second portion P2 of the object OBJ.

Figure 2A:
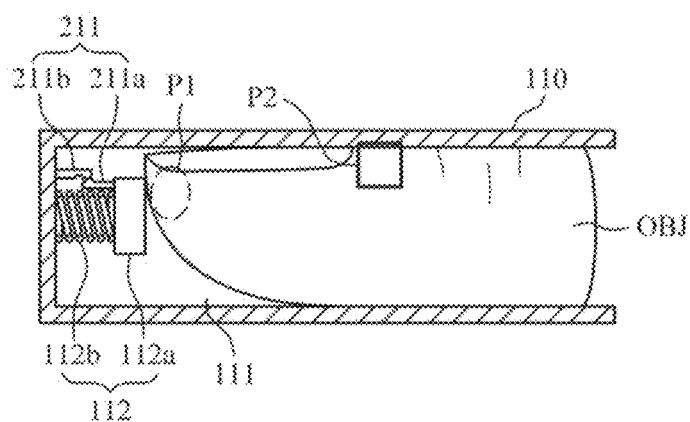
FIGS. 2A, 2B, and 2C are diagrams for describing example embodiments of an interface.
Figure 2B:
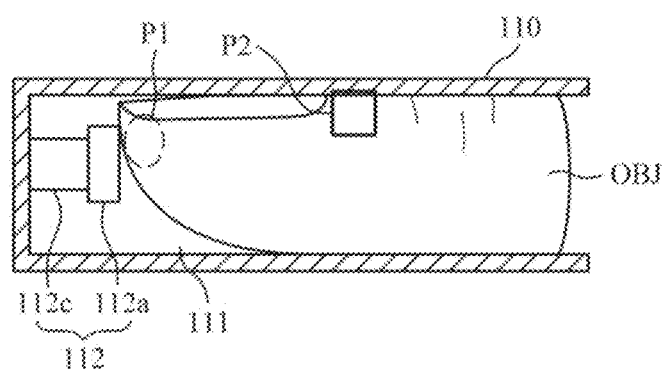
Figure 2C:
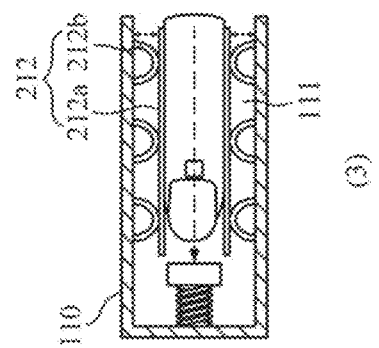
Figure 2C:
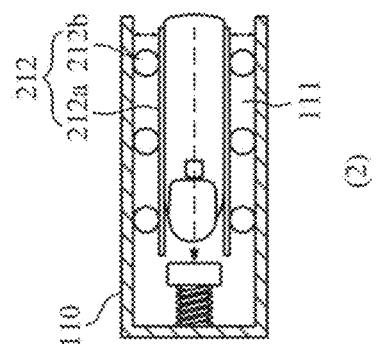
Figure 2C:
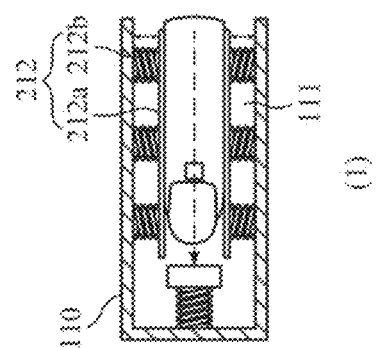

FIGS. 2A to 2C are diagrams for describing example embodiments of an interface housing.

Referring to FIG. 2A, the pressurizing part 112 of the interface 110 may include a plate 112a with which the first portion P1 is in contact when the object OBJ enters the guide part 111, and an elastic member 112b provided between the interface housing 110 and the plate 112a. The plate 112a may be formed to contact 50% or more of the cross-sectional area of the first portion P1 of the object OBJ, and may be formed in various shapes, such as a circle, a rectangle, and the like. Also, the elastic member 112b may include a spring, rubber, and the like, but is not limited thereto. In this case, the elastic member 112b may be formed to have an elastic coefficient that allows the first portion P1 of the object OBJ to apply a force of at least 3 Newtons (N) or greater to the plate 112a.

In addition, the interface housing 110 may further include a braking part 211 that prevents the plate 112a from moving as the elastic member 112b contracts by the force manually applied by the first portion P1 of the object OBJ in contact with the plate 112a. The braking part 211 may include a first locking part 211a connected to the plate 112a and a second locking part 211b connected to the interface housing 110. The first locking part 211a may include a projection formed on one side thereof and the second locking portion 211b includes a groove formed thereon. Accordingly, the first locking part 211a is moved together as the plate 112a is moved and the projection formed on the first locking part 211a is coupled to the groove formed on the second locking part 211b. In this manner, the movement of the plate 112a may be prevented. However, the structure of the braking part 211 is not limited to that shown in FIG. 2A. The braking part 211 may be formed to adjust the braking position of the plate 112a and may allow the second portion P2 of the object OBJ to be positioned on a lower side of the measurer 120 regardless of the characteristic of the object OBJ such as, for example, the size of a finger.

Referring to FIG. 2B, the pressurizing part 112 of the interface housing 110 may include a plate 112a with which the first portion P1 of the object OBJ is in contact when the object OBJ enters the guide part 111 and an actuator 112c provided between the interface housing 110 and the plate 112a. The plate 112a may be formed to contact 50% or more of the cross-sectional area of the first portion P1 of the object OBJ, and may be formed in various shapes, such as a circle, a rectangle, and the like. There is no particular limitation on the driving method of the actuator 112c, and the driving method may include a motor-based method, an encoder-based method, a piezo-based method, or the like.

When the first portion P1 of the object OBJ is in contact with the plate 112a, the actuator 112c may automatically press the first portion P1 by driving the plate 112a according to a predetermined control signal. In this case, the control signal may be generated by a device (hereinafter referred to as a "control device") that is connected to the optical apparatus 100 in a wireless or wired manner or that includes the optical apparatus 100. In this case, information regarding a driving range, or the like, of the plate 112a may be preset based on the characteristic of the object OBJ and stored in a storage of the control device, and the control device may generate the control signal for controlling the actuator 112c based on the information in the storage regarding the driving range, or the like.

FIG. 2C is a diagram illustrating top views of example embodiments of the interface housing 110.

Referring to FIG. 2C, the interface housing 110 may further include a support part 212 that supports lateral sides of the object when the object enters the guide part 111. The support part 212 may include a support 212a in contact with the object and an elastic body 212b that is deformed according to the thickness and/or shape of the object. In this case, the elastic member 212b may be formed of a spring (as shown in (1)), ball-shaped rubber (as shown in (2)), a clip (as shown in (3)), or the like, but these are merely examples. The support part 212 may fix the lateral side of the object as the widths of both supports 212a are adjusted according to the thickness and/or shape of the object, and thus the center of pressurizing part 112 and the center of the first portion of the object may coincide with each other.

Figure 3A:
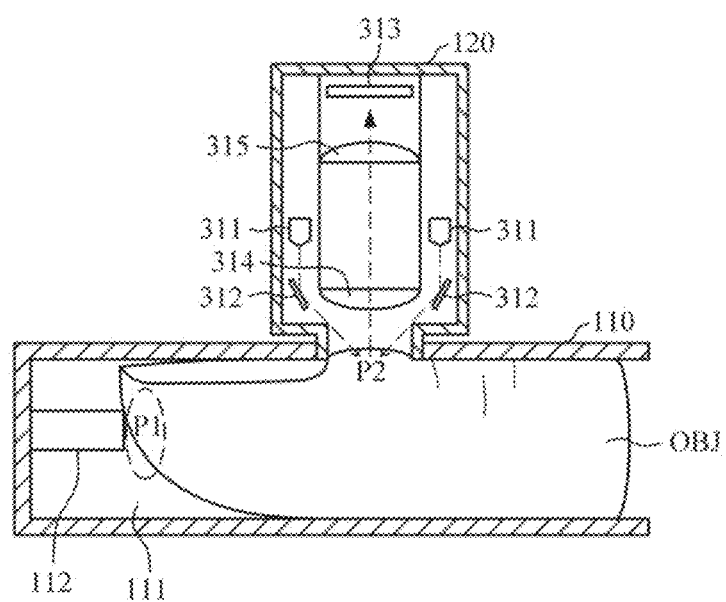
FIGS. 3A, 3B, and 3C are diagrams for describing example embodiments of a measurer.
Figure 3B:
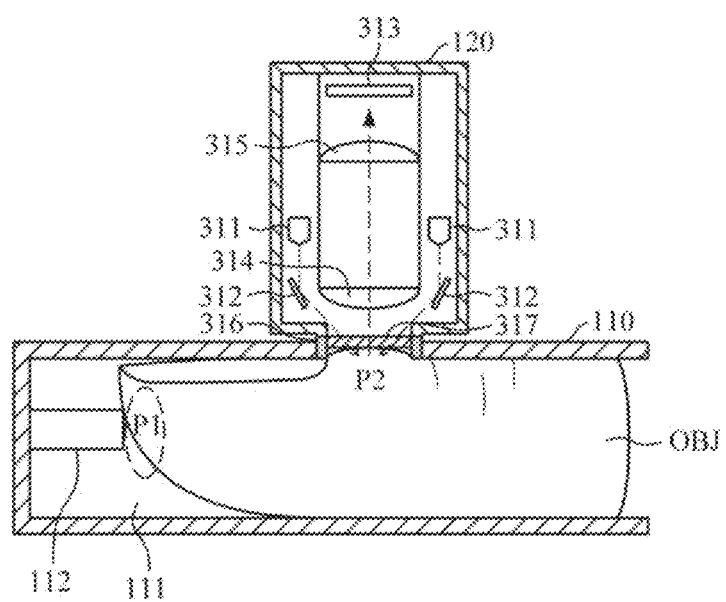
Figure 3C:
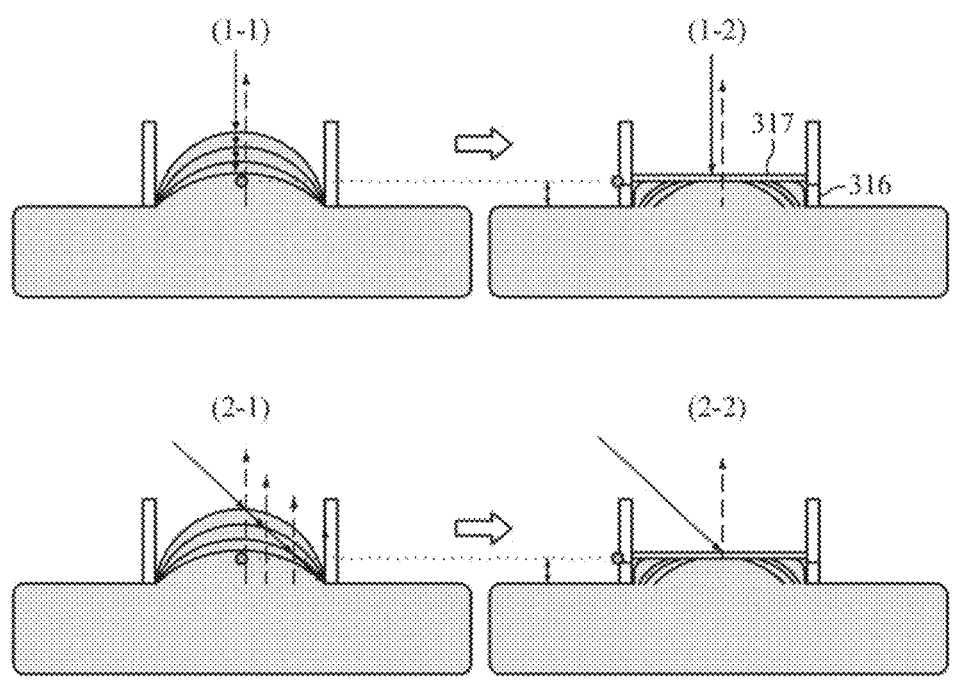

FIGS. 3A to 3C are diagrams for describing example embodiments of a measurer.

FIG. 3A schematically illustrates an embodiment of the measurer 120. Referring to FIG. 3A, the measurer 120 may measure a bio-signal from the second portion P2 that is disposed above an upper side of the interface housing 110 and protrudes as the first portion P1 of the object OBJ is pressed by the pressurizing part 112.

The measurer 120 may include light sources 311 and 312 that emit light to the second portion P2 of the object OBJ, and detectors 313, 314, and 315 that detect light scattered from the object OBJ. As shown, the light sources 311 and 312 may be provided in an off-axis configuration on the side surfaces of the detectors 313, 314, and 315, and may emit light to the second portion P2 of the object OBJ in the lateral direction. However, aspects of the present disclosure are not limited thereto, and the light sources 311 and 312 and the detectors 313, 314, and 315 may be provided in an on-axis configuration.

The light source 311 may include one or more light emitting bodies. The light emitting bodies may emit light of different wavelengths. Also, the light source 312 may include a reflecting mirror that adjusts the light emitted by the light emitting body to a desired focal direction of the second portion P2. In this case, the reflecting mirror may be rotatable to adjust an irradiation direction of light.

The detectors 314 and 315 may include one or more condensing lenses that condense light emitted from the second portion P2 of the object OBJ. In this case, the condensing lenses may be collimating lenses, focusing lenses, or the like. The detector 313 may include a light receiver that receives light condensed by the condensing lenses, or the like. The light receiver may include a single photodiode, a photodiode array, an image sensor, or the like. In addition, the detector 313 may further include a fiber connected to the light receiver, a waveguide, grating, or the like.

FIG. 3B schematically illustrates another example embodiment of the measurer 120. Referring to FIG. 3B, the measurer 120 may measure a bio-signal from the second portion P2 that is disposed above an upper side of the interface housing 110 and protrudes as the first portion P1 of the object OBJ is pressed by the pressurizing part 112.

The measurer 120 may include a hollow body 316 provided on a lower portion thereof that is in contact with the object OBJ. The hollow body 316 may include a hollow-shaped tube, such as an O-ring or a spacer. At least a portion of the second portion P2 may be accommodated in the hollow body 316 as the first portion P1 of the object OBJ is pressed by the pressurizing part 112. In this case, the height or thickness of the hollow body 316 may be configured according to the elasticity or viscous characteristic of the object OBJ. For example, the height or thickness of the hollow body 316 may be configured based on the maximum protruding height and/or the minimum protruding height of the second portion P2 that protrudes as the first portion P1 is pressed, and the height or thickness of the hollow body 316 may be configured to be less than, for example, the minimum protruding height.

In addition, an optical window 317 may be provided on an upper side of the hollow body 316 on the lower portion of the measurer 120. The optical window 317 may be made of a material that transmits light such as, for example, quartz, magnesium fluoride (MgF2), calcium fluoride (CaF2), borosilicate crown glass (e.g., BK7), zinc selenide (ZnSe), etc. However, the optical window 317 is not limited thereto. The optical window 317 may be in contact with the second portion P2 of the object OBJ and flattens a protruding portion so that the light source is prevented from deviating from the focal length even when the protruding height of the second portion P2 changes according to the measurement time. Also, the optical window 317 may prevent drying of the skin surface due to the evaporation of moisture by laser heat.

For example, (1-1) and (1-2) of FIG. 3C illustrate an on-axis configuration in which incident light and emitted light are parallel to each other. In the case (1-1) where the hollow body 316 and the optical window 317 are not provided, the protruding height of the second portion P2 gradually decreases over time, which leads to deviation from the focal length, and accordingly, the intensity of a measured spectrum may gradually decrease. In the case (1-2) where the hollow body 316 and the optical window 317 are provided, it is possible to minimize a phenomenon in which the light source deviates from the focal length even when the protruding height of the second portion P2 changes according to the measurement time, and thereby the performance of a measured signal may be improved.

(2-1) and (2-2) of FIG. 3C illustrate an off-axis configuration in which incident light is not parallel to emitted light. In the case (2-1) where the hollow body 316 and the optical window 317 are not provided, the focal position of the second portion P2 may change over time both in a vertical direction and in a horizontal direction so that the performance of a measured signal may be further reduced. In the case (2-2) where the hollow body 316 and the optical window 317 are provided, the protruding height of the second portion P2 is maintained constant according to the measurement time and hence the performance and intensity of a measured spectrum signal may be maintained constant.

Figure 4A:
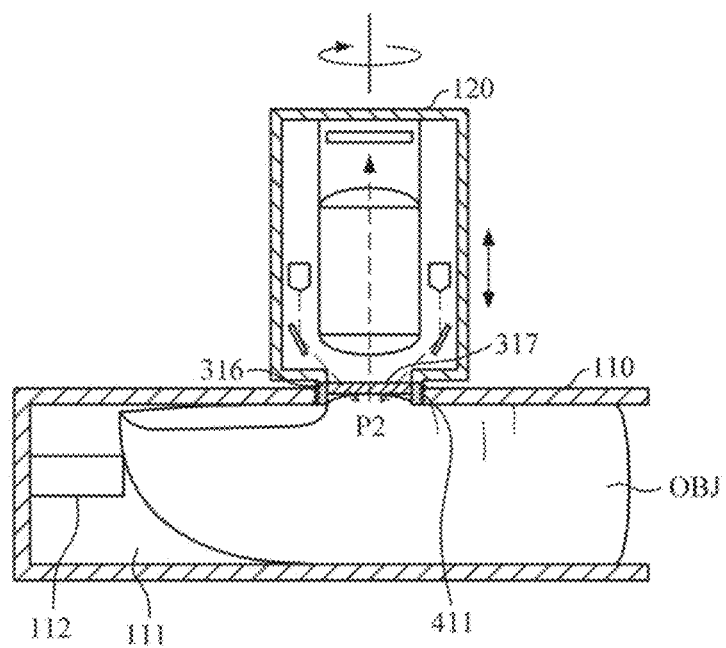
FIGS. 4A, 4B, and 4C are diagrams for describing example embodiments in which the measurer is moved.
Figure 4B:
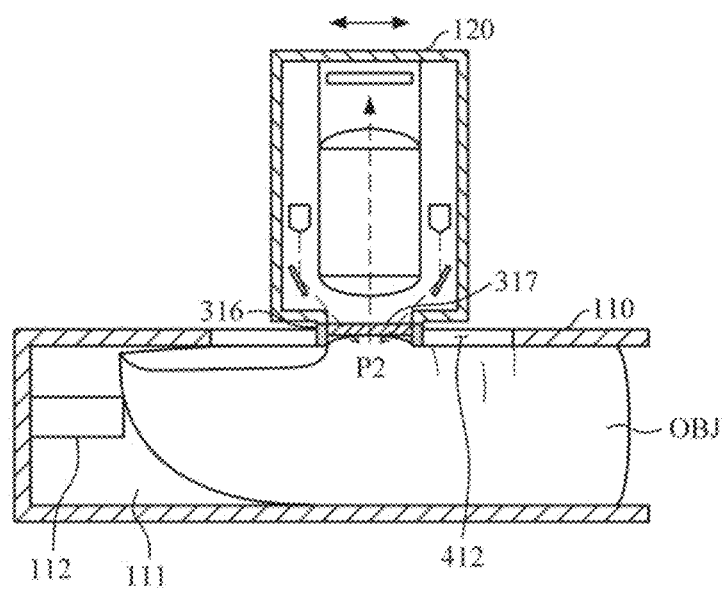
Figure 4C:
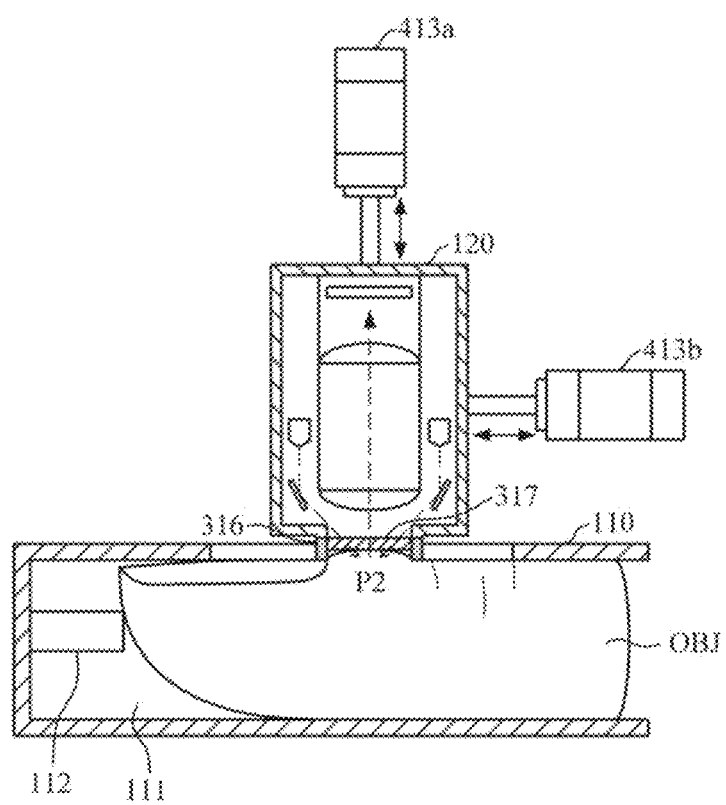

FIGS. 4A to 4C are diagrams for describing example embodiments in which the measurer is moved. As shown, the measurer 120 may be provided on an upper side of the interface housing 110 and may be movable in a vertical direction and/or a horizontal direction.

Referring to FIG. 4A, the measurer 120 and the interface housing 110 may be coupled to each other via screw coupling 411. In this case, the measurer 120 may be rotated manually by a user or rotated automatically under the control of the control device, thereby moving in a vertical direction. In this way, by adjusting the height of the measurer 120, a contact pressure between the measurer 120 and the second portion of the object OBJ may be adjusted. In this case, when the optical apparatus 100 includes the force/pressure sensor 130 on the lower side of the interface housing 110 as shown in FIG. 1B, the user or the control device may adjust the height of the measurer 120 on the basis of the force or pressure measured by the force/pressure sensor 130 so that the contact pressure between the measurer 120 and the second portion is maintained at a preset contact pressure.

Referring to FIG. 4B, the measurer 120 and the interface housing 110 may be coupled to each other through a guard rail 412, or the like, and the measurer 120 may be moved in a horizontal direction manually by the user or automatically according to the control of the control device. For example, when a finger is seated in the guide part 111, the position of the second portion may be slightly different depending on various factors, such as the length or thickness of the finger, the size of a fingernail, and the like, and hence the position of the measurer 120 may be adjusted in a horizontal direction so that the lower portion of the measurer 120 can accurately contact the second portion of the object.

Referring to FIG. 4C, actuators 413a and 413b may be provided on an upper side and a lateral side of the measurer 120, and the position of the measurer 120 may be automatically adjusted by the actuators 413a and 413b. In this case, information regarding a driving range, or the like, of the measurer 120 may be preset in a storage of the control device, and the control device may generate the control signal for controlling the actuators 413a and 413b on the basis of the driving range information set in the storage.

Figure 5:
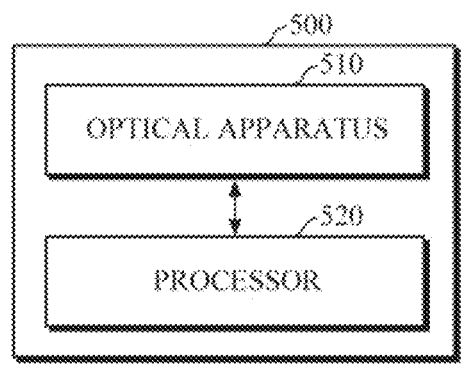
FIG. 5 is a block diagram illustrating an apparatus for estimating bio-information according to an example embodiment.

FIG. 5 is a block diagram illustrating an apparatus for estimating bio-information according to an example embodiment.

Referring to FIG. 5, an apparatus for estimating bio-information may include an optical apparatus 510 and a processor 520.

The optical apparatus 510 includes an interface housing and a measurer. The interface housing may include a guide part and a pressurizing part. The guide part is provided to minimize (or reduce) spectral interference caused by external factors, such as a change in the position of an object and/or a change in the elasticity of a measurement site, etc., during the measurement time, rather than the actual change in a measured component inside the blood vessel, and the pressurizing part presses a predetermined portion of the object to congest the measurement site of the object. The pressurizing part may press the predetermined portion of the object to stop the pulse caused by the blood flow at the measurement site, thereby reducing noise, and as the measurement site becomes congested, the capillary thickness increases and the blood volume increases, which may increase a scattered light signal. The measurer may acquire a spectrum signal by emitting light to the measurement site of the object and detecting light scattered or reflected from the measurement site of the object. The optical apparatus 510 is described in detail with reference to FIGS. 1A to 4C, and hence a description thereof will be omitted hereinafter.

The processor 520 may be connected to the optical apparatus 510 via wired or wireless communication. Based on receiving a request for estimating bio-information, the processor 520 may control an output interface to output information that guides a user to seat the object in the interface housing of the optical apparatus 510.

The processor 520 may control the optical apparatus 510 by generating a control signal for controlling the optical apparatus 510. For example, when the object is seated in the interface housing, the processor 520 may automatically adjust a position of a measurer by generating a control signal for controlling the position of the measurer, or may control an output interface to output information that guides a user to manually adjust the position of the measurer. Based on receiving force/pressure data between the measurer and the object from a force/pressure sensor, the processor 520 may control the height of the measurer on the basis of the received force/pressure data so that the contact pressure between the measurer and the object can be maintained constant.

Also, when the position of the measurer is adjusted to be in contact with the measurement site of the object, the processor 520 may drive light sources of the measurer. When the light source includes a plurality of light emitting bodies, the light emitting bodies may be driven sequentially or simultaneously through time-division.

Based on receiving the spectrum signal from the optical apparatus 510, the processor 520 may analyze the received spectrum signal to estimate bio-information. In this case, the bio-information may include oxygen saturation, carotenoids, blood sugar, sugar intake, triglycerides, cholesterol, calories, protein, body water, extracorporeal water, uric acid, alcohol, and the like. However, the bio-information is not limited thereto. For example, the processor 520 may estimate bio-information on the basis of absorbance data by using a predefined bio-information estimation model. In this case, the bio-information estimation model, which defines a correlation between absorbance by wavelength and bio-information, may be generated in advance through training using absorbance by wavelength acquired from a plurality of users and measured values of correct bio-information as training data. The bio-information estimation model may be generated as a linear or non-linear function equation using machine learning, a neural network, artificial intelligence, or the like.

Figure 6:
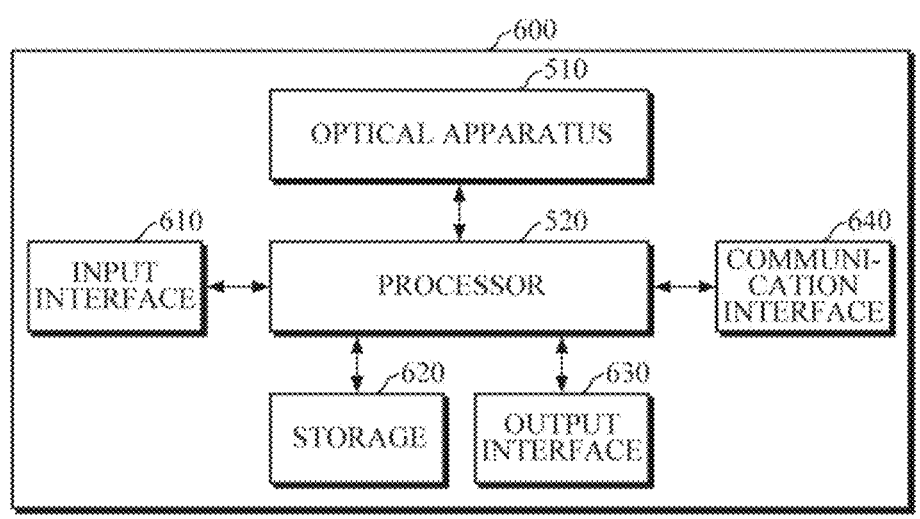
FIG. 6 is a block diagram illustrating an apparatus for estimating bio-information according to another example embodiment.

FIG. 6 is a block diagram illustrating an apparatus for estimating bio-information according to another example embodiment.

Referring to FIG. 6, an apparatus 600 for estimating bio-information according to another example embodiment may include an optical apparatus 510, a processor 520, an input interface 610, a storage 620, an output interface 630, and a communication interface 640. The optical apparatus 510 and the processor 520 are described in detail above, and thus descriptions thereof will not be reiterated hereinafter.

The input interface 610 may receive commands and/or data to be used for each component of the apparatus 600 such as, for example, the processor 520, from a user or an external device. The input interface 610 may include a microphone, a mouse, a keyboard, a touch screen, and/or a digital pen (such as a stylus pen), but is not limited thereto.

The storage 620 may store information related to driving of the optical apparatus 510, (e.g., information regarding a horizontal/vertical movement range of a measurer, conditions for driving a light source, and the like) and/or reference information (e.g., a bio-information estimation model, characteristic information of a user, and the like) related to bio-information estimation. In this case, the user's characteristic information may include a health condition, gender, age, or the like, of the user. Also, the storage 620 may store data which is generated and/or processed by various components of the apparatus 600 for estimating bio-information. The storage 620 may include a storage medium, such as a flash memory, a hard disk, a multimedia card micro, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like, but is not limited thereto.

The output interface 630 may externally output the data generated or processed by various components of the apparatus 600 for estimating bio-information. For example, the output interface 630 may include an acoustic output device to externally output an acoustic signal. An acoustic output module may include a speaker and/or a receiver. Also, the output interface 630 may include a display device to externally provide data in a visual manner. The display device may include a display, a hologram device, or a projector. The display device may include a touch circuitry set to sense a touch and/or a sensor circuitry (e.g., a pressure sensor, etc.) set to measure a magnitude of a force generated by a touch. Also, the output interface 630 may include a haptic module to output data through tactile sensation or vibration. The haptic module may convert an electrical signal into a mechanical stimulation (e.g., vibration, motion, etc.) or an electrical stimulation that the user is able to recognize through a tactile sensation or kinesthetic sensation. The haptic module may include a motor, a piezoelectric element, and/or an electrical stimulation device.

The communication interface 640 may communicate with an external device to transmit the data generated and/or processed by the apparatus 600 for estimating bio-information to the external device, and may receive data to be used by the apparatus 600 for estimating bio-information from the external device. The external device may include an information processing device, such as a smartphone, a tablet personal computer (PC), a desktop computer, a laptop computer, or the like. The communication interface may communicate with the external device by using various wired or wireless communication techniques including Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, the communication techniques are not limited thereto.

The example embodiments can be implemented by computer-readable code stored in a non-transitory computer-readable medium and executed by a processor. Code and code segments constituting the computer program can be inferred by a computer programmer skilled in the art. The non-transitory computer-readable medium includes all types of recording media in which computer-readable data are stored. Examples of the non-transitory computer-readable medium include a ROM, a RAM, a CD-ROM, a magnetic tape, a floppy disk, and an optical data storage. Further, a recoding medium may be implemented in the form of a carrier wave such as Internet transmission. In addition, the non-transitory computer-readable medium may be distributed to computer systems over a network, in which computer readable code may be stored and executed in a distributed manner.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An optical apparatus comprising:
   an interface housing comprising:
     a guide part defined by an interior space of the interface housing and configured to guide an object to a measurement position; and
     a pressurizing part configured to induce congestion of a second portion of the object by pressing a first portion of the object when the object is disposed within the guide part; and
   a measurer comprising:
     a light source provided on an upper side of the guide part and configured to emit light to the second portion of the object when the object is at the measurement position; and
     a detector provided on the upper side of the guide part and configured to measure a bio-signal from the second portion by detecting light scattered or reflected from the second portion,
   wherein the pressurizing part comprises:
     a plate configured to contact the first portion of the object; and
     an elastic member that is connected to the plate and configured to deform as the first portion presses the plate,
   wherein the interface housing further comprises a braking part configured to reduce movement of the plate caused by pressing of the first portion of the object, and
   wherein the braking part comprises:
     a first locking part connected to the plate and including a projection; and
     a second locking part connected to the interface housing and having a groove configured to couple to the projection based on the first locking part being moved.

2. The optical apparatus of claim 1, wherein the object is a finger, the first portion is a fingertip, and the second portion is a nailfold.

3. The optical apparatus of claim 1, wherein the plate is configured to contact at least 50% of a cross-sectional area of the first portion.

4. The optical apparatus of claim 1, wherein the elastic member has an elastic coefficient that allows the object to apply a force of at least 3 Newtons to the plate.

5. The optical apparatus of claim 1, wherein the pressurizing part comprises:
   an actuator configured to pressurize the first portion by driving the plate when the first portion is in contact with the plate.

6. The optical apparatus of claim 1, wherein the interface housing further comprises a support part configured to support a lateral side of the object when the object is disposed in the guide part.

7. The optical apparatus of claim 6, wherein the support part comprises an elastic body configured to deform according to a thickness and a shape of the object.

8. The optical apparatus of claim 1, wherein the measurer comprises a hollow body configured to accommodate at least a portion of the second portion that protrudes as the pressurizing part presses the first portion of the object.

9. The optical apparatus of claim 8, wherein a height of the hollow body is less than a minimum protruding height of the second portion.

10. The optical apparatus of claim 8, wherein the measurer further comprises an optical window provided on an upper side of the hollow body and configured to contact the protruding second portion.

11. The optical apparatus of claim 8, wherein the measurer is configured to be movable in a horizontal direction or in a vertical direction.

12. The optical apparatus of claim 11, further comprising a sensor provided on a lower side of the interface housing and configured to measure a force or a pressure applied to the second portion by vertical movement of the measurer.

13. The optical apparatus of claim 1, wherein the light source comprises a rotatable reflecting mirror configured to emit light to a focal position on the second portion.

14. The optical apparatus of claim 1, wherein the detector further comprises a condensing lens configured to condense the light scattered or reflected from the second portion.

15. An apparatus for estimating bio-information, the apparatus comprising:
   an optical apparatus configured to:
     induce congestion of a second portion of an object by pressing a first portion of the object; and
     measure a bio-signal from the second portion; and
   a processor configured to estimate the bio-information based on the bio-signal,
   wherein the optical apparatus comprises:
     an interface housing comprising:
       a guide part defined by an interior space of the interface housing and configured to guide the object to a measurement position; and
       a pressurizing part configured to induce the congestion of the second portion of the object by pressing the first portion when the object is disposed in the guide part; and
     a measurer, comprising a light source and a detector, provided on an upper side of the guide part and configured to measure the bio-signal from the second portion when the object is at the measurement position,
   wherein the pressurizing part comprises:
     a plate configured to contact the first portion of the object; and an elastic member that is connected to the plate and configured to deform as the first portion presses the plate, wherein the interface housing further comprises a braking part configured to reduce movement of the plate caused by pressing of the first portion of the object, and wherein the braking part comprises:
- a first locking part connected to the plate and including a projection; and
- a second locking part connected to the interface housing and having a groove configured to couple to the projection based on the first locking part being moved.

16. The apparatus of claim 15, wherein the bio-information comprises at least one of oxygen saturation, carotenoids, blood sugar, sugar intake, triglycerides, cholesterol, calories, protein, body water, extracorporeal water, uric acid, and alcohol.

17. The apparatus of claim 15, wherein the object is a finger, the first portion is a fingertip, and the second portion is a nailfold.

\* \* \* \* \*